(12) United States Patent
Futatsugi

(10) Patent No.: US 10,191,006 B2
(45) Date of Patent: Jan. 29, 2019

(54) HUMIDITY SENSOR

(71) Applicant: SII Semiconductor Corporation, Chiba-shi, Chiba (JP)

(72) Inventor: Toshiro Futatsugi, Chiba (JP)

(73) Assignee: ABLIC INC. (JP)

(*) Notice: Subject to any disclaimer, the term of this patent is extended or adjusted under 35 U.S.C. 154(b) by 79 days.

(21) Appl. No.: 15/050,843

(22) Filed: Feb. 23, 2016

(65) Prior Publication Data
US 2016/0258894 A1 Sep. 8, 2016

(30) Foreign Application Priority Data
Mar. 4, 2015 (JP) .................................. 2015-042467

(51) Int. Cl.
*G01N 27/22* (2006.01)

(52) U.S. Cl.
CPC .................................. *G01N 27/223* (2013.01)

(58) Field of Classification Search
CPC .................................................... G01N 27/223
USPC ...................................................... 73/335.04
See application file for complete search history.

(56) References Cited

U.S. PATENT DOCUMENTS 7,176,700 B2 * 2/2007 Itakura ................ G01N 27/223
324/670
2006/0048572 A1 * 3/2006 Isogai .................. G01N 27/223
73/335.04
2007/0186649 A1 * 8/2007 Sudo ..................... G01N 27/223
73/335.04

OTHER PUBLICATIONS

English translation of Japanese Publication No. 2003-516539, Publication Date May 13, 2003.
English translation of Japanese Publication No. 2007-192622, Publication Date Aug. 2, 2007.
English translation of Japanese Publication No. 2014-167445, Publication Date Sep. 11, 2014.

* cited by examiner

*Primary Examiner* — Hezron E Williams
*Assistant Examiner* — Rodney T Frank
(74) *Attorney, Agent, or Firm* — Adams & Wilks

(57) ABSTRACT

A humidity sensor includes an insulating film formed on a semiconductor substrate, and a plurality of first electrodes and a plurality of second electrodes arranged on the insulating film so that each first electrode is adjacent to four of the second electrodes in four directions of up, down, right, and left when viewed in plan view, while each second electrode is adjacent to four of the first electrodes in four directions of up, down, right, and left when viewed in plan view. Metal wiring embedded in the insulating film electrically connects one of the first electrodes to another of the first electrodes, and electrically connects one of the second electrodes to another of the second electrodes. The humidity sensor has increased capacitance per unit area and improved adhesiveness and can be made using normal semiconductor manufacturing processes.

15 Claims, 7 Drawing Sheets

—— Electrical Line of Force
------- Equipotential line

HUMIDITY SENSOR

BACKGROUND OF THE INVENTION

1. Field of the Invention

The present invention relates to a humidity sensor, and more particularly, to a capacitive humidity sensor.

2. Description of the Related Art

A structure in which electrodes for capacitance measurement are formed on a semiconductor substrate and covered with a humidity sensitive film has been known as a related-art capacitive humidity sensor. The humidity sensitive film is characterized by having a dielectric constant that varies depending on the level of humidity, and detects a change in humidity from a change in capacitance between the electrodes. FIG. 9 is a diagram for illustrating an example of the sectional structure of the humidity sensitive film. An insulating film 2 is formed on a substrate 1, and a plurality of capacitance measurement electrodes 3a and a plurality of capacitance measurement electrodes 3b are formed on the insulating film 2. A thin protective film 4 is configured to cover surfaces of the electrodes in order to secure the reliability of the electrodes, and a thick humidity sensitive film 5 is configured to cover the protective film 4.

Known arrangement patterns of the capacitance measurement electrodes 3a and 3b according to the related art are illustrated in FIG. 10A to FIG. 10C. In FIG. 10A, two electrodes, namely, one electrode 3a and one electrode 3b, are arranged in a comb-teeth pattern (see Japanese Patent Translation Publication No. 2003-516539, for example). In FIG. 10B, a plurality of electrodes 3a each aligned to form an island shape are surrounded by the other electrode 3b (see Japanese Patent Application Laid-open No. 2007-192622, for example). The electrodes 3a each forming an island shape are electrically connected to one another through lower-layer wiring 6a. In FIG. 10C, a plurality of columnar electrodes 3a and a plurality of columnar electrodes 3b are aligned to form an equilateral triangle grid (see Japanese Patent Application Laid-open No. 2014-167445, for example). The columnar electrodes 3a are electrically connected to one another through the lower-layer wiring 6a, and the columnar electrodes 3b are electrically connected to one another through lower-layer wiring 6b.

The comb-teeth wiring structure of FIG. 10A has an advantage in that the structure is high in capacitance per unit area and can be formed with a single layer of wiring. However, the layout slanted toward a particular direction may cause the humidity sensitive film to peel easily under stress applied in the particular direction. In addition, the structure has a weakness with regards to the ease of embedding in that a void is likely to, form when the humidity sensitive film is embedded in the case where the capacitance measurement electrodes 3a and 3b are desirably formed thick and a narrow space is desirably set between the electrodes in order to secure a desired capacitance in a limited area.

The structure of FIG. 10B is an electrode arrangement that has fourfold symmetry, and therefore has less chance for the humidity sensitive film to peel with respect to a particular direction. However, the likelihood of a void being formed in this structure is about the same as in the comb-teeth wiring structure of FIG. 10A. The structure of FIG. 10B is lower in capacitance per unit area than the comb-teeth wiring structure of FIG. 10A.

The structure of FIG. 10C is an electrode arrangement that has sixfold symmetry, and therefore has less chance of peeling with respect to a particular direction. The structure of FIG. 10C is also improved in the ease of embedding of the humidity sensitive film because the humidity sensitive film is pinched more lightly between the electrodes 3a and 3b than as in FIG. 10A and FIG. 10B. However, the structure of FIG. 10C is not higher in capacitance per unit area than the comb-teeth wiring structure as described later, despite the fact that the columnar electrodes are formed at the closest packing density. In addition, the manufacturing cost rises in the case where the columnar electrodes 3a and 3b are manufactured by a dedicated process (see Japanese Patent Application Laid-open No. 2014-167445, for example) that may not match with a normal semiconductor manufacturing process. In the case where signal processing circuits and the humidity sensor are built on the same semiconductor chip, forming the electrodes 3a and 3b of the humidity sensor in a step of manufacturing wiring of the signal processing circuits is desirable in order to keep the manufacturing cost from increasing.

SUMMARY OF THE INVENTION

It is therefore an object of the present invention to provide a humidity sensor that is increased in capacitance per unit area and is improved in the close adhesiveness and ease of embedding of a humidity sensitive film, while being capable of fitting into normal semiconductor manufacturing processes.

As a measure for solving the problems described above, according to one embodiment of the present invention, there is provided a humidity sensor in which capacitance measurement electrodes 3a and 3b are each aligned to form an island shape, and each electrode 3a (or 3b) of one type is arranged so as to be adjacent to electrodes 3b (or 3a) of another type in four directions of up, down, right, and left when viewed in plan view. The electrodes 3a (or electrodes 3b) are electrically connected to one another through a via and lower-layer wiring.

According to the one embodiment of the present invention, the capacitance measurement electrodes of the humidity sensor may be formed by a normal semiconductor manufacturing process and, because the humidity sensitive film is pinched more lightly between the capacitance measurement electrodes than in the related art such as the comb-teeth wiring structure, the ease of embedding of the humidity sensitive film is also improved. The present invention where the electrode layout is not slanted toward a particular direction also has less chance for the humidity sensitive film to peel. Moreover, the present invention is higher in capacitance per unit area than the related art in which the columnar electrodes are aligned to form the equilateral triangle grid.

DETAILED DESCRIPTION OF THE INVENTION

Figure 1:
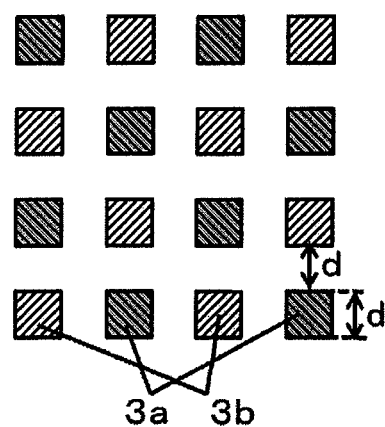
FIG. 1 is a diagram for illustrating the arrangement of capacitance measurement electrodes in a humidity sensor of the present invention.

In a humidity sensor of the present invention, capacitance measurement electrodes are each aligned to form an island shape and, as illustrated in FIG. 1, each electrode 3a (or 3b) of one type is arranged so as to be adjacent to electrodes 3b (or 3a) of another type in four directions of up, down, right, and left when viewed in plan view except in the perimeter of the arrangement. This electrode arrangement is used in embodiments of the present invention on which a concrete and detailed description is given below.

First Embodiment

Figure 2A:
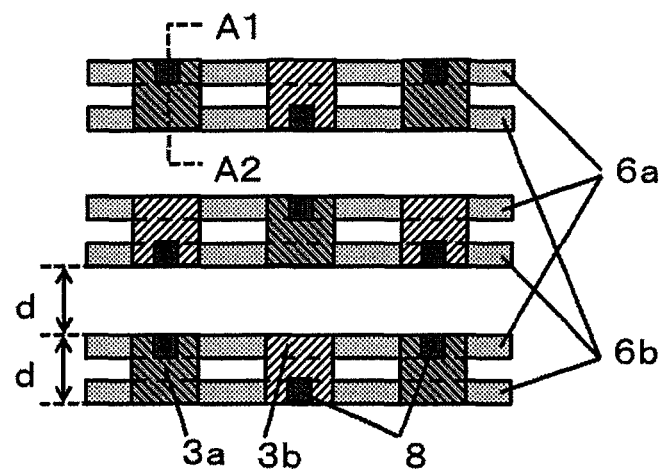
FIG. 2A is a plan view of a first embodiment of the present invention.
Figure 2B:
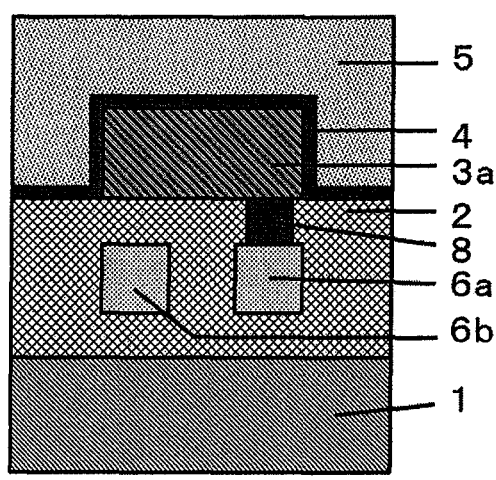
FIG. 2B is a sectional view of the first embodiment of the present invention.

A first embodiment of the present invention is illustrated in FIG. 2A and FIG. 2B. FIG. 2A is a plan view in which the capacitance measurement electrodes 3a and 3b viewed from above are each shaped like a square that measures a length d on a side and, as illustrated in FIG. 1, are arranged so that the space between one capacitance measurement electrode 3a and one capacitance measurement electrode 3b that are adjacent to each other is also d. Each electrode is connected to one of lower-layer wiring 6a and lower-layer wiring 6b through a via 8, and humidity can be detected by measuring a capacitance that is generated between all of the electrodes 3a and all of the electrodes 3b. The lower-layer wiring 6a and the lower-layer wiring 6b are arranged side by side under the capacitance measurement electrodes 3a and 3b that are adjacent to one another, and the placement of the via 8 in each capacitance measurement electrode 3a differs from the placement of the via 8 in each capacitance measurement electrode 3b.

FIG. 2B is a sectional view taken along the line A1-A2 of FIG. 2A. An insulating film 2 is formed on a semiconductor substrate 1, and the capacitance measurement electrodes 3a and 3b are formed on the insulating film 2. The lower-layer wiring 6a and the lower-layer wiring 6b are formed in the insulating film 2. Each electrode 3a (or 3b) is connected to the wiring 6a (or 6b) through the via 8. The lower-layer wiring 6a and the lower-layer wiring 6b, the via 8, and the electrodes 3a and 3b are formed by a normal semiconductor manufacturing process. Multi-layer wiring is usually used in the manufacture of signal processing circuit portions, which means that no additional manufacturing step is needed until the forming of the electrodes 3a and 3b. The electrodes 3a and 3b are covered with a thin protective film 4, which in turn is covered with a thick humidity sensitive film 5. The protective film can be, for example, a SiN film having a thickness of 100 nm. An organic material that varies in dielectric constant depending on the level of humidity, for example, can be used for the humidity sensitive film. The steps of forming the protective film and the humidity sensitive film are steps added for the humidity sensor.

Figure 3:
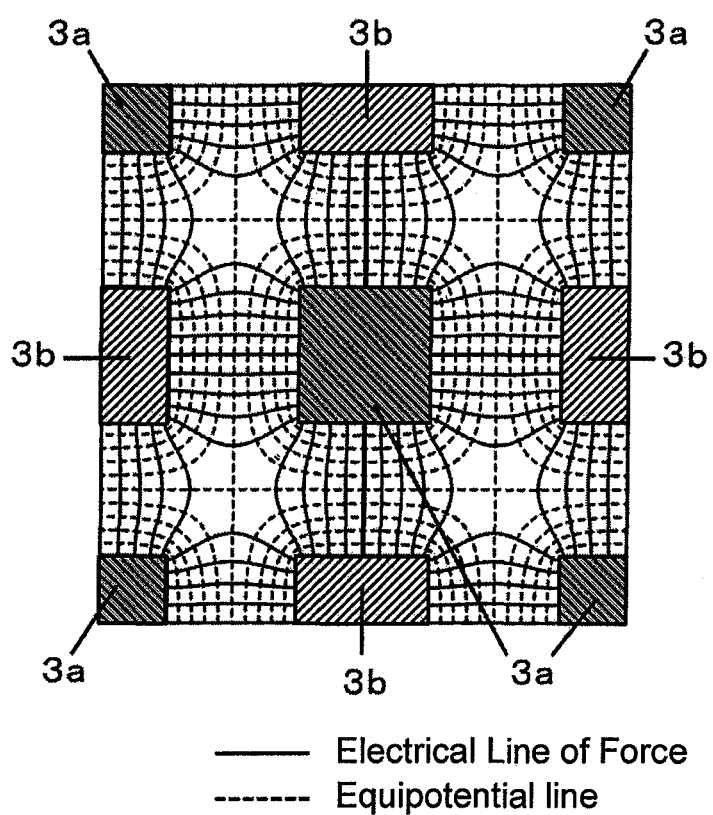
FIG. 3 is a diagram for illustrating results of numerical calculation of electrical lines of force and equipotential lines in the electrode arrangement of the present invention.

In order to confirm that the electrode arrangements of FIG. 1 and FIG. 2A and FIG. 2B are increased in capacitance per unit area, the capacitance was calculated by numerical calculation that uses a two-dimensional model. FIG. 3 is a diagram for illustrating results of performing the numerical calculation of electrical lines of force and equipotential lines when a voltage is applied in this electrode arrangement. Similar numerical calculation was performed for various electrode arrangements to calculate the capacitance, and results of comparison between the electrode arrangement of this embodiment and the other electrode arrangements are shown in Table 1.

TABLE 1

| Structure | Capacitance ratio |
| --- | --- |
| Comb-teeth wiring (FIG. 10A) | 1.00 |
| Island structure (FIG. 10B) | 0.78 |
| Equilateral triangle grid (FIG. 10C) | 0.99 |
| Present invention (FIGS. 1, 2A and 2B) | 1.28 |
| Fourth embodiment (FIG. 6) | 1.01 |
| Sixth embodiment (FIG. 8) | 1.02 |

Figures 10A, 10B, 10C:
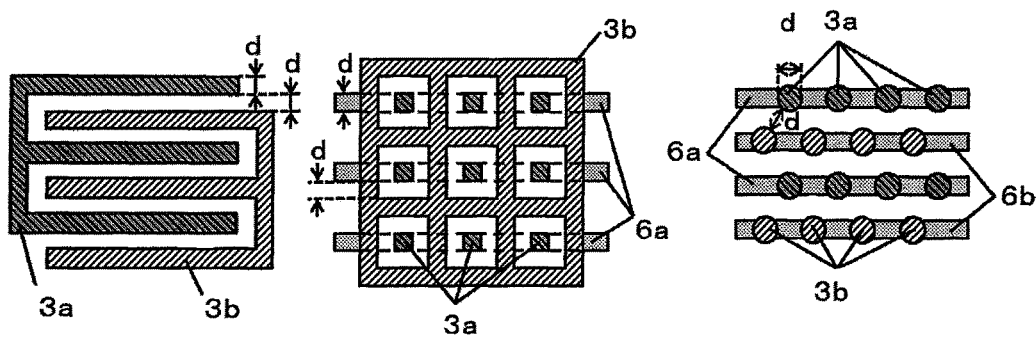
FIG. 10A to FIG. 10C are arrangement patterns of capacitance measurement electrodes in humidity sensors of the related art.

In the calculation, the capacitance per unit area was obtained with the dimension d in the drawing of each wiring structure set to the same value. Table 1 compares the capacitance in each wiring structure against the capacitance in the comb-teeth wiring structure. The capacitance per unit area in the present invention is 1.28 times higher than that in the comb-teeth wiring structure (FIG. 10A). The capacitance in the equilateral triangle grid alignment (FIG. 10C) is 0.99 times higher than that in the comb-teeth wiring structure, which is substantially the same as the capacitance in the comb-teeth wiring structure, despite the fact that this alignment is a closest-packed structure. It is therefore understood that an effective way to increase the capacitance per unit area is to give each electrode a shape as close as possible to a rectangular shape and to arrange each electrode of one type to be adjacent to the electrodes of the other type in four directions of up, down, right, and left when viewed in plan view.

Second Embodiment

Figure 4:
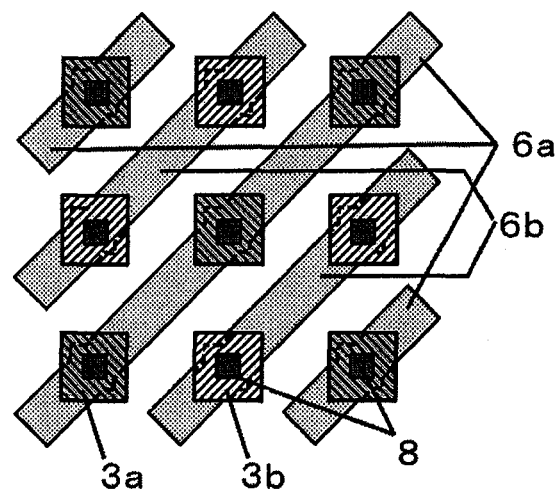
FIG. 4 is a plan view of a second embodiment of the present invention.

A second embodiment of the present invention is illustrated in FIG. 4. In the second embodiment, the alignment of the capacitance measurement electrodes 3a and 3b are the same as in the first embodiment, but the layout of the lower-layer wiring 6a and the lower-layer wiring 6b differs from the first embodiment. The layout in the first embodiment, where two pieces of lower-layer wiring are laid out immediately under each row of capacitance measurement electrodes, cannot always be employed due to restrictions put by layout rules that do not allow the line width of and a space between pieces of lower-layer wiring to be small enough in the case where a humidity sensor is manufactured by a semiconductor manufacturing process. In such cases, tilting the layout of the lower-layer wiring 6a and the lower-layer wiring 6b by 45 degrees as in the second embodiment may widen the wiring width and the wiring space enough to become free of the restrictions put by layout rules.

Third Embodiment

Figure 5:
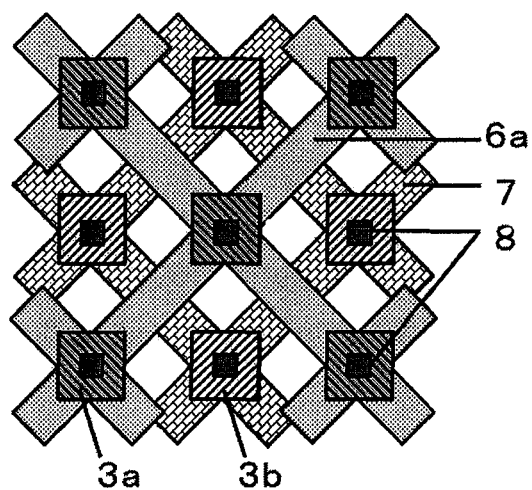
FIG. 5 is a plan view of a third embodiment of the present invention.

A third embodiment of the present invention is illustrated in FIG. 5. In the third embodiment, the alignment of the capacitance measurement electrodes 3a and 3b are the same as in the first embodiment and the second embodiment, but the layout of the lower-layer wiring 6a and the lower-layer wiring 6b differs from the first embodiment and the second embodiment in that two layers of lower-layer wiring are used. Each electrode 3a is electrically connected to the lower-layer wiring 6a through the via 8. Each electrode 3b is electrically connected through the via 8, the lower-layer wiring 6b (that is immediately below the electrode 3b and therefore is not shown), and a via (not shown) under the wiring 6b to second lower-layer wiring 7. In the case where the signal processing circuits use three or more layers of wiring, the structure of the third embodiment can be manufactured without requiring additional steps.

Fourth Embodiment

Figure 6:
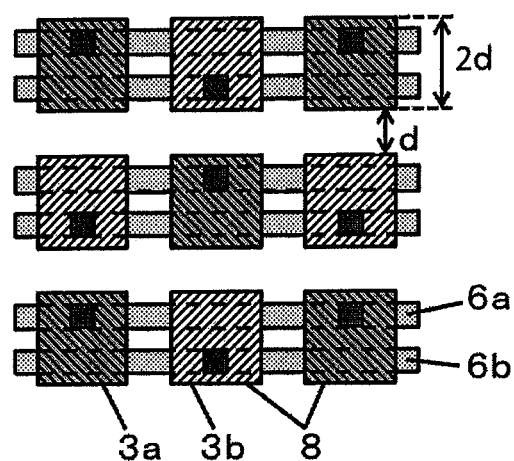
FIG. 6 is a plan view of a fourth embodiment of the present invention.

A fourth embodiment of the present invention is illustrated in FIG. 6. In the first embodiment to the third embodiment, the length of one side of each of the capacitance measurement electrodes 3a and 3b is the same as the distance between one electrode and another, and the proportion of the area taken up by the electrodes to the entire area (metal occupancy) is thus 25%. A certain metal occupancy is required in semiconductor manufacturing processes in order to process electrodes properly, and a metal occupancy of 25% is insufficient in some cases. In the fourth embodiment, the metal occupancy is raised by setting the length of one side of each capacitance measurement electrode to twice the distance between one electrode and another. The metal occupancy in this case is 44%, which causes no problem in electrode processing. Although the capacitance per unit area in this embodiment is lower than in other embodiments, about the same level of capacitance as the one in the comb-teeth wiring structure can be secured in this embodiment as shown in Table 1.

Fifth Embodiment

Figure 7:
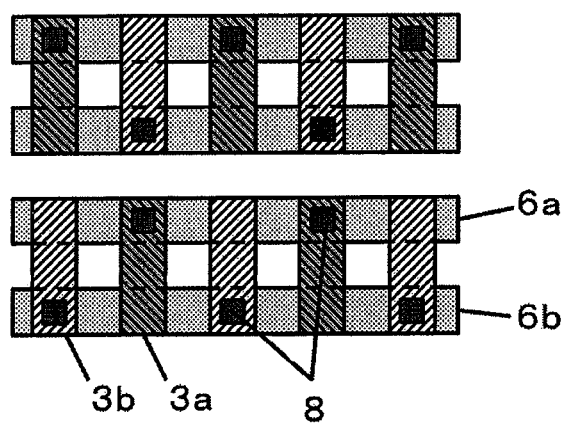
FIG. 7 is a plan view of a fifth embodiment of the present invention.

A fifth embodiment of the present invention is illustrated in FIG. 7. Each of the capacitance measurement electrodes 3a and 3b in the fifth embodiment has a rectangular shape instead of a square shape. With this layout also, the chance for the humidity sensitive film to peel is lessened and the ease of embedding of the humidity sensitive film is improved without dropping the capacitance per unit area.

Sixth Embodiment

Figure 8:
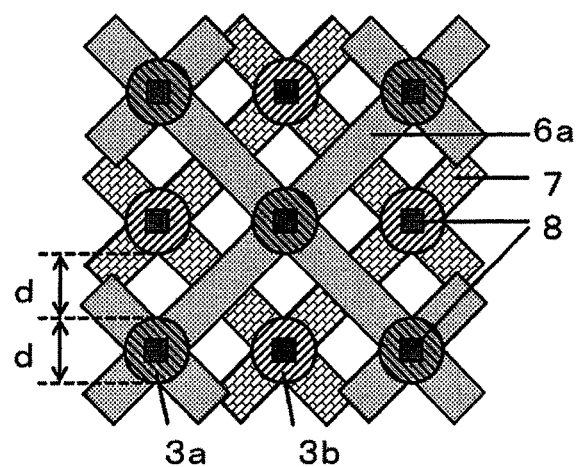
FIG. 8 is a plan view of a sixth embodiment of the present invention.
Figure 9:
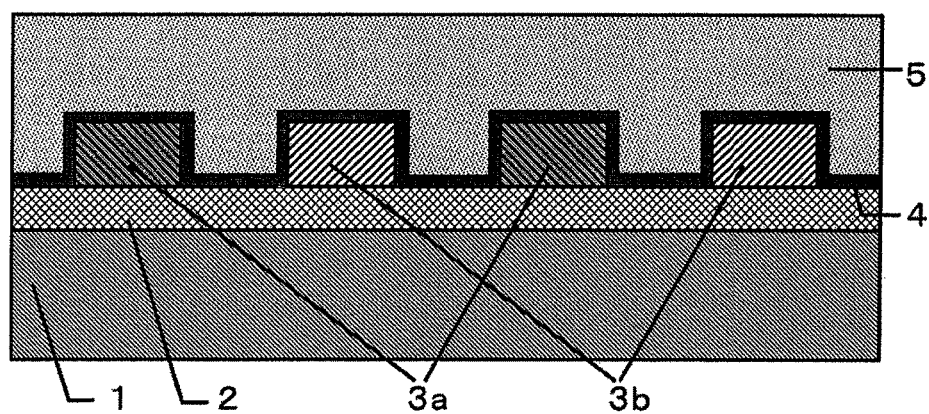
FIG. 9 is a sectional view of a capacitance measuring portion in a humidity sensor of the related art.

A sixth embodiment of the present invention is illustrated in FIG. 8. Each of the capacitance measurement electrodes 3a and 3b in the sixth embodiment has a circular shape in top view. Giving each electrode a rectangular shape and arranging each rectangular electrode of one type adjacent to rectangular electrodes of the other type along the four sides are desirable in order to simply obtain a high capacitance. In order to increase the capacitance per unit area, on the other hand, reducing the size of each electrode and the space between electrodes is also desirable. This embodiment discusses a case in which the shape of each electrode is close to a circle instead of a rectangle as a result of advancing the miniaturization. The capacitance in this embodiment is slightly higher than the capacitance in the equilateral triangle grid alignment as shown in Table 1. It is therefore understood that, even when the shape of each electrode is circular as in this case, an arrangement in which each electrode of one type is adjacent to electrodes of the other type in four directions of up, down, right, and left when viewed in plan view, is advantageous in securing the capacitance.

What is claimed is:

1. A humidity sensor, comprising:
a semiconductor substrate;
an insulating film formed on a surface of the semiconductor substrate;
a plurality of first electrodes and a plurality of second electrodes, both formed on the insulating film and arranged so that each of the plurality of first electrodes is adjacent to one of the plurality of second electrodes in each of four directions of up, down, right, and left when viewed in plan view, while each of the plurality of second electrodes is adjacent to one of the plurality of first electrodes in each of four directions of up, down, right, and left when viewed in plan view, except in a perimeter of the arrangement;
a first metal wiring completely embedded in the insulating film and electrically connecting, through a via, one of the plurality of first electrodes to another one of the plurality of first electrodes;
a second metal wiring completely embedded in the insulating film and electrically connecting, through a via, one of the plurality of second electrodes to another one of the plurality of second electrodes; and
a humidity sensitive film formed on the plurality of first electrodes and the plurality of second electrodes.

2. A humidity sensor according to claim 1, wherein the first metal wiring and the second metal wiring are arranged below the plurality of first electrodes, and are arranged below the plurality of second electrodes as well.

3. A humidity sensor according to claim 1, wherein the first metal wiring and the second metal wiring are formed from different wiring layers.

4. A humidity sensor according to claim 1, wherein the each of the plurality of first electrodes and the each of the plurality of second electrodes have a rectangular shape.

5. A humidity sensor according to claim 4, wherein the each of the plurality of first electrodes and the each of the plurality of second electrodes have a square shape.

6. A humidity sensor according to claim 4, wherein the first metal wiring and the second metal wiring are aligned in directions oblique to directions of sides of the rectangle.

7. A humidity sensor according to claim 1, wherein the each of the plurality of first electrodes and the each of the plurality of second electrodes are larger in size than a space between one of the plurality of first electrodes and one of the plurality of second electrodes.

8. A humidity sensor, comprising:
a semiconductor substrate;
an insulating film formed on a surface of the semiconductor substrate;
a plurality of first electrodes and a plurality of second electrodes, which are formed on the insulating film and are arranged so that four of the plurality of second electrodes are arranged in four directions of up, down, right, and left of each of the plurality of first electrodes, while four of the plurality of first electrodes are arranged in four directions of up, down, right, and left of each of the plurality of second electrodes, except in a perimeter of the arrangement;
a first wiring completely embedded in the insulating film and connecting, through vias, the plurality of first electrodes to one another;

a second wiring completely embedded in the insulating film and connecting, through vias, the plurality of second electrodes to one another; and a humidity sensitive film formed on the plurality of first electrodes and the plurality of second electrodes, wherein each of the plurality of first electrodes and each of the plurality of second electrodes are a square having a side of length d, wherein a space between one of the plurality of first electrodes and one of the plurality of second electrodes that are adjacent to each other is d, and wherein the humidity sensor has a capacitance ratio per unit area higher than a capacitive humidity sensor that has a comb-teeth wiring structure in which a wiring width is d and a wiring space is d.

9. A humidity sensor, comprising:

a semiconductor substrate;

an insulating film formed on a surface of the semiconductor substrate;

an arrangement of first electrodes and second electrodes all formed on the insulating film and arranged so that each first electrode is adjacent to one of the second electrodes in each of four directions of up, down, right, and left when viewed in plan view, and each second electrode is adjacent to one of the first electrodes in each of four directions of up, down, right, and left when viewed in plan view, except for the first and second electrodes situated around a perimeter of the arrangement;

a first metal wiring completely embedded in the insulating film for electrically connecting, through a via, one first electrode to another first electrode;

a second metal wiring completely embedded in the insulating film for electrically connecting, through a via, one second electrode to another second electrode; and a humidity sensitive film formed on the first electrodes and the second electrodes.

10. A humidity sensor according to claim 9, wherein the first metal wiring and the second metal wiring are arranged below the first electrodes and below the second electrodes.

11. A humidity sensor according to claim 9, wherein the first metal wiring and the second metal wiring are different wiring layers.

12. A humidity sensor according to claim 9, wherein the each of the first electrodes and each of the second electrodes has a rectangular shape.

13. A humidity sensor according to claim 12, wherein each of the first electrodes and each of the second electrodes has a square shape.

14. A humidity sensor according to claim 12, wherein the first metal wiring and the second metal wiring are aligned in directions oblique to directions of sides of the rectangle.

15. A humidity sensor according to claim 9, wherein each of the first electrodes and each of the second electrodes is larger in size than a space between one of the first electrodes and one of the second electrodes.

* * * * *